(12) United States Patent
Putman

(10) Patent No.: US 9,567,110 B1
(45) Date of Patent: Feb. 14, 2017

(54) SATELLITE TESTBED FOR EVALUATING CRYOGENIC-LIQUID BEHAVIOR IN MICROGRAVITY

(71) Applicant: Sierra Lobo, Inc., Milan, OH (US)

(72) Inventor: Philip Travis Putman, Huron, OH (US)

(73) Assignee: SIERRA LOBO, INC., Milan, OH (US)

( * ) Notice: Subject to any disclaimer, the term of this patent is extended or adjusted under 35 U.S.C. 154(b) by 256 days.

(21) Appl. No.: 14/306,987

(22) Filed: Jun. 17, 2014

Related U.S. Application Data

(60) Provisional application No. 61/835,838, filed on Jun. 17, 2013.

(51) Int. Cl.
  *B64G 1/10* (2006.01)
(52) U.S. Cl.
  CPC ..................... *B64G 1/105* (2013.01)
(58) Field of Classification Search
  CPC ...................................................... B64G 1/105
  USPC .............................................. 73/53.01, 61.41
  See application file for complete search history.

(56) References Cited

U.S. PATENT DOCUMENTS

| | | | | |
|---|---|---|---|---|
| 4,553,917 A | * | 11/1985 | Lee | B22F 9/008 |
| | | | | 219/121.65 |
| 6,374,618 B1 | | 4/2002 | Lak | |
| 7,559,508 B1 | * | 7/2009 | Taylor | B64G 1/002 |
| | | | | 244/159.4 |
| 2002/0056790 A1 | * | 5/2002 | Trimmer | B64G 1/50 |
| | | | | 244/171.7 |
| 2002/0066825 A1 | * | 6/2002 | Miralles | B64C 1/30 |
| | | | | 244/49 |
| 2003/0051486 A1 | * | 3/2003 | Ursan | F04B 15/08 |
| | | | | 62/50.6 |
| 2004/0188562 A1 | * | 9/2004 | Mueller | B64G 1/002 |
| | | | | 244/10 |
| 2010/0000232 A1 | * | 1/2010 | Valentian | B64G 1/402 |
| | | | | 62/6 |
| 2014/0216066 A1 | * | 8/2014 | Snyder | F17C 13/021 |
| | | | | 62/49.2 |

OTHER PUBLICATIONS

Chato, David J., and William J. Taylor. "Small Experiments for the Maturation of Orbital Cryogenic Transfer Technologies." World Space Congress (1992): Washington, D.C.

Chato, David J. "Experimentation for the Maturation of Deep Space Cryogenic Refueling Technologies." Tech. No. 2008-214929. Cleveland: NASA Glenn Research Center, 2008.

\* cited by examiner

*Primary Examiner* — Michael A Lyons
*Assistant Examiner* — Suman K Nath
(74) *Attorney, Agent, or Firm* — Pearne & Gordon LLP

(57) ABSTRACT

Provided is a testbed for conducting an experiment on a substance in a cryogenic liquid state in a microgravity environment. Such a testbed includes a frame with rectangular nominal dimensions, and a source section supported by the frame for supplying the substance to be evaluated in the cryogenic liquid form. An experiment supported by the frame includes an experiment vessel in fluid communication with the storage tank to receive and condense the substance into the cryogenic liquid state. A sensor senses a property of the cryogenic liquid in the experiment vessel as part of the experiment, and a bus section includes a controller configured to control delivery of the substance to the experiment vessel, and receives property data indicative of the property sensed by the sensor for subsequent evaluation on Earth.

19 Claims, 9 Drawing Sheets

Stowed Configuration

In the stowed configuration, two sepals are folded behind each of the four solar panels. An elastic element connects one of each pair of sepals to an adjacent solar panel. The elastic element fits into a slot in the rails of the primary structure. The solar panels are mounted to spring-loaded hinges. The panels are held in place either by the inside of surface of the deployer or by a release mechanism. The panels and sepals are held together using flexible tape, located on the side opposite incident sunlight.

The sepals are composed of a material that reflects in the solar and Earth infrared spectra, e.g. aluminized mylar. The elastic element must be composed of a material that remains elastic in the orbital environment.

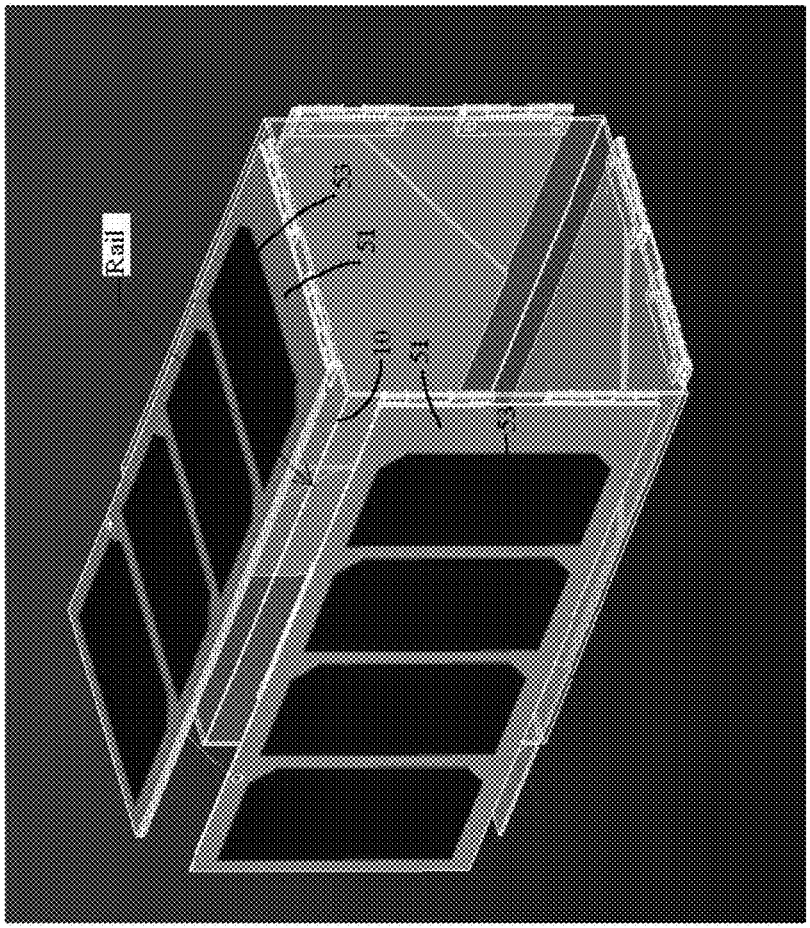

FIG. 7

SATELLITE TESTBED FOR EVALUATING CRYOGENIC-LIQUID BEHAVIOR IN MICROGRAVITY

CROSS-REFERENCE TO RELATED APPLICATIONS

This application claims the benefit of U.S. Provisional Application No. 61/835,838, filed Jun. 17, 2013, which is incorporated in its entirety herein by reference.

BACKGROUND OF THE INVENTION

1. Field of the Invention

This application relates generally to a method and apparatus for evaluating fluid behavior as part of a scientific experiment and, more specifically, to a testbed and testing method of evaluating the behavior of a cryogenic liquid in a microgravity environment. The testbed can be a miniaturized (e.g. CubeSat) satellite testbed that can be launched into low-Earth orbit as a secondary payload aboard a rocket or other vehicle capable of leaving Earth's atmosphere, and that carries an experiment for evaluating cryogenic-liquid behavior in microgravity.

2. Description of Related Art

Cryogenic liquids are vital to the continued exploration and exploitation of space, particularly for missions beyond Earth's orbit. For example, liquid cryogens are used as rocket fuel for propulsion of spacecraft. Certain cryogens, e.g. liquid oxygen, are densified forms of atmospheric gases suitable for human respiration that may prove invaluable for storage on long space missions, for example a manned mission to Mars. These cryogens must be stored in tanks carried by the spacecraft for use as-needed, e.g. for thrust, maneuvering, course adjustment or breathing.

The behavior of liquid cryogens in storage tanks within the atmosphere and subject to Earth's gravity has been studied and is well understood. But despite the importance cryogens currently play and will continue to play in orbital and beyond-orbital space missions, there is little data concerning the behavior of liquid cryogens in a micro-gravity environment. Such data would be useful to the design and execution of both orbital and long-range spaceflight missions where liquid cryogens are or will be stored onboard a spacecraft for use during the mission.

A key hurdle to studying the behavior of cryogenic liquids in space is cost. A recent estimate to construct and launch a satellite-based testbed to evaluate cryogenic-liquid behavior was $100 to $200 million. To this point, the associated high cost has stood in the way of this important work. There is accordingly a need for an economical and practical satellite testbed for evaluating cryogenic-liquid behavior in a microgravity environment.

BRIEF SUMMARY OF THE INVENTION

According to one aspect, the subject application involves a testbed for conducting an experiment in a microgravity environment on a substance in a cryogenic liquid state. Such a testbed includes a frame with rectangular nominal dimensions, and a source section supported by the frame. The source section includes a storage tank that stores a compressed gas comprising the substance to be evaluated in the cryogenic liquid form. An experiment section is also supported by the frame and includes an experiment vessel in fluid communication with the storage tank to receive the compressed gas from the storage tank and condense the compressed gas into the cryogenic liquid state. A sensor is adapted to sense a property of the cryogenic liquid in the experiment vessel as part of the experiment, and a bus section includes a controller configured to control delivery of the compressed gas from the storage tank to the experiment vessel. The controller is also configured to receive property data indicative of the property sensed by the sensor for subsequent evaluation on Earth.

According to another aspect, the subject application involves a testbed for conducting an experiment in a microgravity environment on a substance in a cryogenic liquid state. Such a testbed includes a frame with rectangular nominal dimensions, and a source section supported by the frame that includes a source material made, at least in part, of the substance to be evaluated in the cryogenic liquid form. An experiment section is supported by the frame and includes an experiment vessel that receives the substance from the source material and condenses the substance into the cryogenic liquid state. A sensor is adapted to sense a property of the cryogenic liquid in the experiment vessel as part of the experiment. A bus section includes a controller configured to control delivery of the substance to the experiment vessel, and to receive property data indicative of the property sensed by the sensor for subsequent evaluation on Earth. An Earth shield is also coupled to the frame adjacent to the experiment vessel, and includes a plurality of adjustable panels that, when fully deployed, at least partially define a cavity in which the experiment vessel is recessed.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein:

FIG. 7 shows a perspective view of a picosatellite comprising a Sun shield and an Earth shield in stowed states;

DETAILED DESCRIPTION OF THE INVENTION

Figure 1:
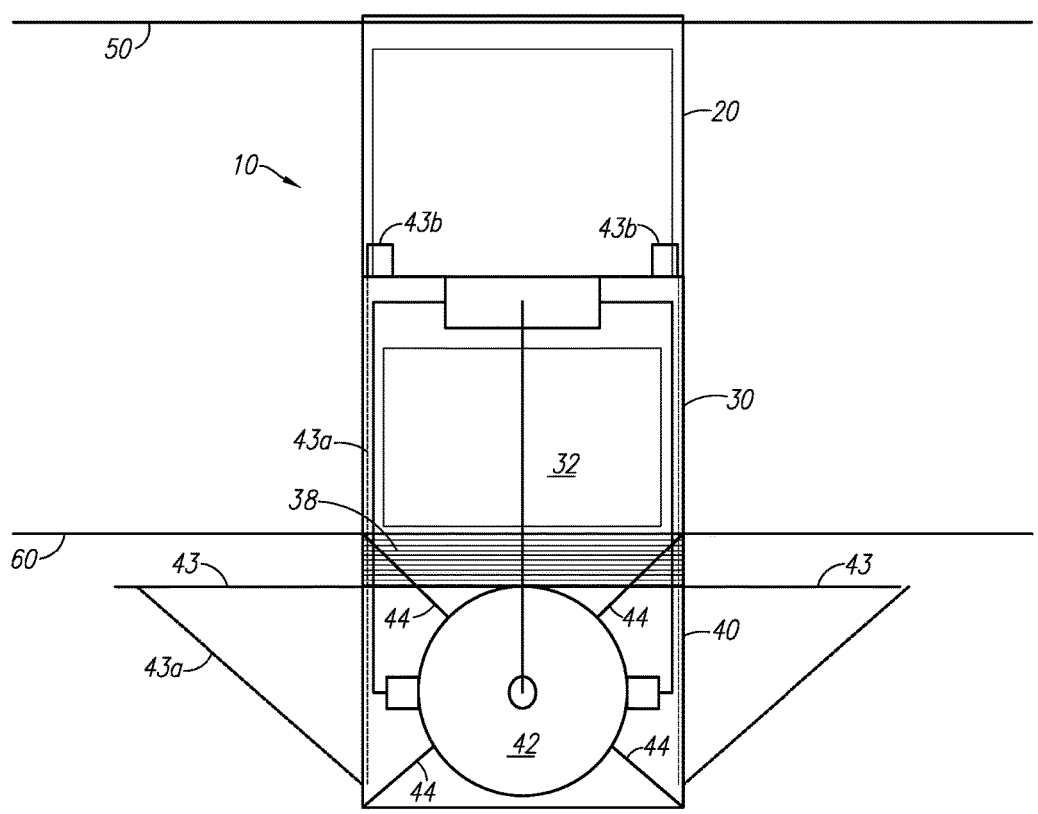
FIG. 1 shows a partially-cutaway side view of an embodiment of a picosatellite.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

CubeSat satellites are picosatellite platforms that can be carried as a secondary payload by vehicles transporting a primary payload into low-Earth orbit or other suitable microgravity environment in which a space-based experiment is to be conducted. Since they are transported as a secondary payload in otherwise unoccupied space aboard a transport vehicle carrying a primary payload, CubeSat satellites enable a broader range of private entities that may not be able to afford the cost to commission a space-bound transport vehicle to deliver a primary payload for conducting space-based research experiments. CubeSats generally include a substantially cube-shaped frame measuring nominally 10 cm×10 cm×10 cm, within the volume of which one can incorporate an experimental apparatus to conduct an experiment in micro-gravity. CubeSats are launched as secondary payloads on other space missions and are deployed by a launcher specially designed to hold the CubeSats during launch and then to deploy them once orbit has been reached. Essentially, the CubeSat launcher rides piggy-back on a launch vehicle whose primary mission is to launch and deploy a primary payload. Such vehicles often have additional available volume beyond the primary payload, which can be sold to CubeSat program participants. As a result, the CubeSat program provides a means of access to space-based experiments at a reasonable cost (because the launch vehicle is going to be launched anyway to deliver the primary payload), which otherwise would be cost-prohibitive for universities and other private researchers.

The present disclosure is directed toward a picosatellite 1, illustrative embodiments of which are shown in FIGS. 1, 4, 5 and 7, capable of being carried as a secondary payload in a conventional CubeSat launcher, e.g. a poly picosatellite orbital deployer ("P-POD"), which includes a rectangular box made of alodined aluminum that can hold up to 340.5 mm×100 mm×100 mm of deployable hardware, aboard a launch vehicle. The P-POD includes a spring-biased door. Once the release mechanism of the P-POD door is actuated, a set of torsion springs at the door hinge swings the door open, and the CubeSats are deployed by the main spring, gliding on internal rails in the P-POD's. The CubeSat launcher utilized with the invention can be a conventional P-POD as known in the art, capable of being loaded aboard and carried into orbit by a conventional launch vehicle. Accordingly, further details concerning the CubeSat launcher and the launch vehicle itself will not be given here.

The present picosatellite 1 includes the form factor of a so-called triple CubeSat configuration so as to be compatible with conventional CubeSat launchers. The triple CubeSat form factor provides adequate space for desired components. A triple CubeSat has nominal dimensions of 100.0 mm×100.0 mm×340.5 mm; i.e. the length and width of a standard CubeSat and a height nominally three times that of a standard CubeSat. The present picosatellite has a frame 10 preferably conforming to the foregoing dimensions. The frame 10 is divided into three sections as seen schematically in FIG. 1, namely: a bus section 20, a gas-generation and/or storage section 30 (interchangeably referred to herein as a source section 30), and an experiment section 40.

The bus section 20 houses the telemetry and control systems for the picosatellite 1. Such systems include, for example, microprocessors programmed with computer-executable instructions for controlling various electronic subsystems aboard the satellite, including position determination, attitude control, experimental-control functions and telemetry for sending and receiving data and control signals between the satellite and a mission-control computer at the Earth's surface.

Embodiments of the source section 30 that generate the gas from a solid source house a gas generator 32 for generating a gas. Briefly, the gas generator 32 contains a solid-form source material for generating a gas from which a desired cryogenic liquid can be condensed. Once the picosatellite 1 is fully deployed in orbit, the cryogenic liquid is ultimately produced from the solid-form source material in order to conduct micro-gravity experiments on the behavior of the liquid as hereafter described. Storing the cryogenic liquid initially in the form of a solid-phase precursor promotes stable storage of the picosatellite 1 to be launched as a secondary payload because it avoids technical and safety challenges associated with storing and maintaining it in the form of either a high-pressure gas or a cryogenic liquid at the time of launch. The latter forms may endanger the launch vehicle or the primary payload in the event of a malfunction, increasing the risk of an accident. Such concerns have been a significant impediment to conducting cryogenic-liquid-behavior experiments in space. Launching such an experiment as a primary-payload satellite has proven prohibitively expensive, and high-pressure gases and cryogenic liquids typically are not permitted as secondary payloads on third-party launch vehicles where the secondary payload could jeopardize the primary payload. The gas generator 32 will be more fully described below.

Figure 8:
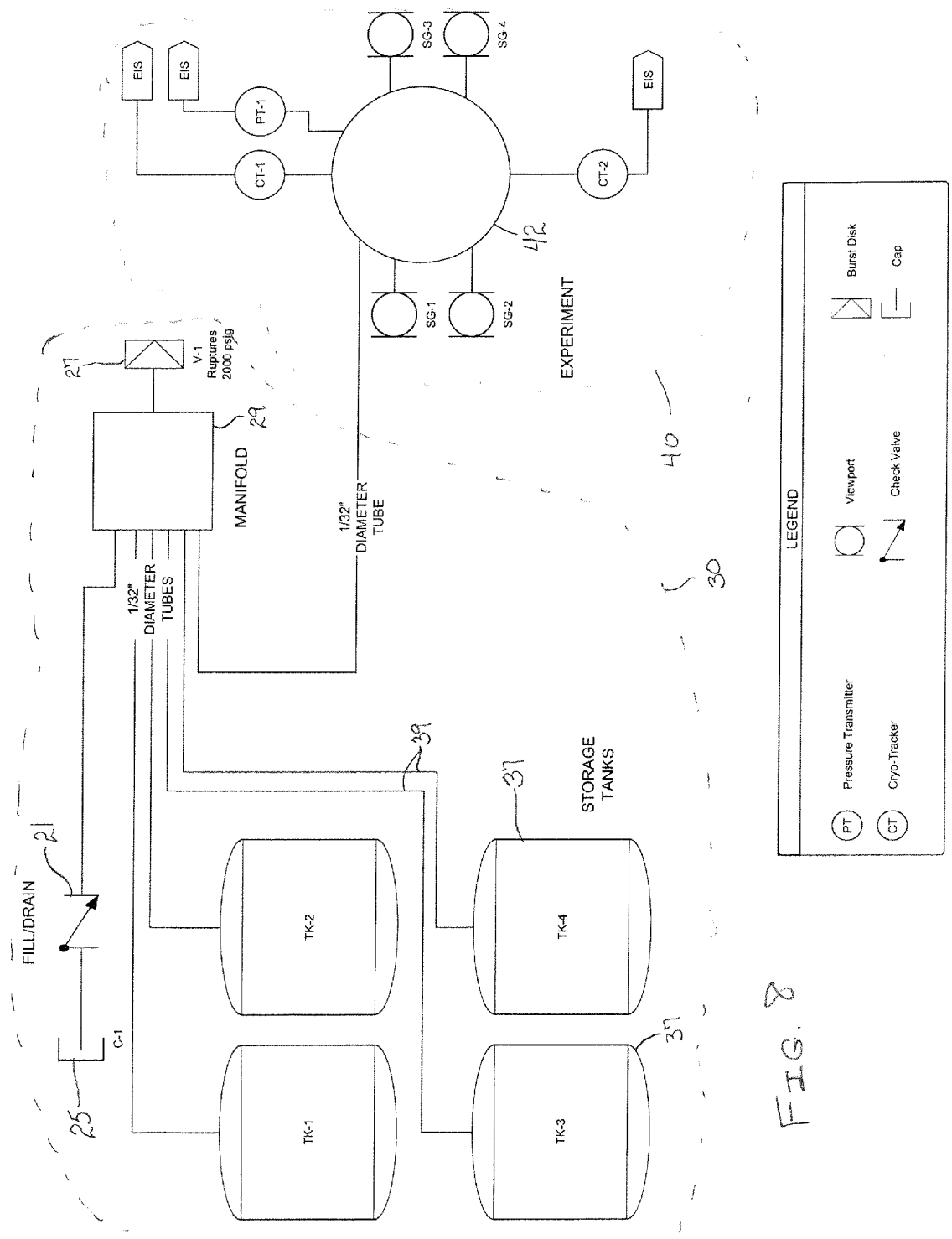
FIG. 8 is a block diagram schematically illustrating an embodiment of a source section including a plurality of storage tanks in fluid communication with an experiment section of a picosatellite.

Alternate embodiments of the source section 30 can include at least one, and optionally a plurality of storage tanks 37, as schematically illustrated in FIG. 8. As shown, the source section 30 includes a plurality (e.g., four) storage tanks 37, each containing a high-pressure gas, cryogenic liquid, or other such material at the time of launch from which the cryogenic liquid that is to be the subject of the microgravity experiment can be supplied to the experiment section 40. Each storage tank 37 is plumbed with tubes 39 of a suitable diameter (e.g., 1/32 in.) leading to a manifold 29 with a separate inlet for each tube 39 in fluid communication with a different storage tank 37. A controller provided to the bus section 20 can be configured to control the delivery of the compressed gas within each storage tank 37 to the experiment vessel 42, concurrently, simultaneously, or sequentially (e.g., a first one of the storage tanks 37 is substantially depleted before the gas from a second one of the storage tanks 37 is delivered to the experiment vessel 42). A burst disk 27 or other suitable measure can optionally be provided in fluid communication with the manifold 29 to protect against the buildup of an excessive pressure and allow the controlled release of the fluid in response to being subjected to a pressure greater than the burst pressure of the burst disk 27. A cap 25 can be adjustably provided to a fill port leading to the interior of the storage tanks 37, allowing the storage tanks 37 to be filled with the desired fluid via the manifold 29 and subsequently sealed so the picosatellite can be transported into low-Earth orbit. A check valve 21 interferes with the ability of the fluid within the storage tanks 37 to escape through the fill port.

The experiment section 40 houses an experiment vessel 42. Once in orbit, the vessel 42 is filled with the desired cryogenic liquid from the gas generated in the gas generator 32 or supplied from the storage tanks 37 of the source section 30. The vessel 42 is fitted with a variety of sensors, including cameras and temperature and liquid-level sensors, which can be used to measure and evaluate liquid-cryogen behavior in the micro-gravity environment of Earth orbit. The vessel 42 and its instrumentation will be more fully described below.

As shown in FIGS. 1 and 4-6, the picosatellite 1 includes a sun shield 50. In orbit, the picosatellite 1 preferably is attitude-controlled so that the sun shield 50 is disposed between the sun and the picosatellite 1, such that the experiment section 40 is positioned distant-most from the sun. In other words, the sun shield 50 is positioned through adjustment of the picosatellite's attitude relative to the sun and/or Earth to shade most, and optionally all of the experiment section 40 during evaluation of the behavior of the cryogenic liquid therein. The sun shield 50 shields the picosatellite 1, and particularly the experiment section 40, from direct irradiation by solar and IR rays emanating from the sun. An Earth shield 60 is also provided immediately above the experiment section 40 (i.e. in the direction along the picosatellite 1 from the experiment section 40 toward the sun shield 50, to be located adjacent to the intersection of the experimental section 40 and the source section 30). The Earth shield 60 insulates the experiment section from IR irradiation from the Earth to a maximum practical extent while in orbit, and is positioned through attitude adjustment of the picosatellite 1 to insulate the experiment section 40 as the picosatellite 1 orbits the Earth. It is located immediately above the experiment section 40 in order to eclipse the Earth as much as possible from the experiment section 40; i.e. to enable the smallest possible exposure window between the Earth and the experiment section 40 through which IR irradiated from Earth may otherwise raise the temperature of the experiment section 40 and of the cryogenic liquid within the vessel 42.

Each of the foregoing features will now be described in more detail.

Figure 2:
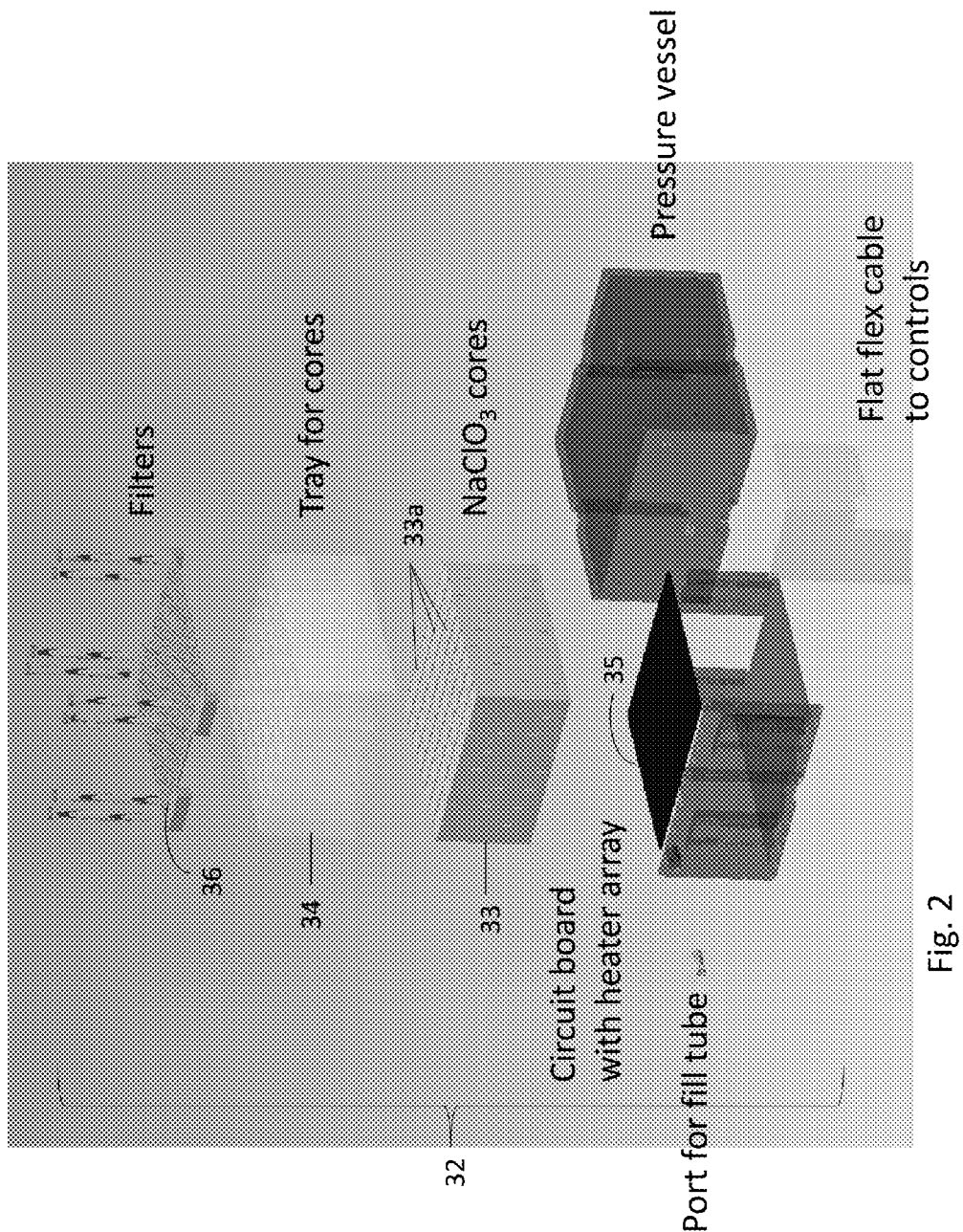
FIG. 2 shows an exploded view of a gas generator provided to an embodiment of a source section of a picosatellite.

Beginning with the gas-generation embodiment of the source section 30, a schematic exploded view of an illustrative embodiment of the gas generator 32 is illustrated in FIG. 2. The gas generator 32 includes an array 33 of solid-form cores comprising a source material for a desired gas. In FIG. 2, the solid-form cores are sodium chlorate ($NaClO_3$), from which gaseous oxygen can be produced as later described. However, solid form cores according to alternate embodiments can be formed, at least in part, by any source material to be examined as a cryogenic liquid in the experiment section 40. In the illustrated embodiment, each of the cores in the array 33 is physically separated from the adjacent cores via a partitioned tray 34. When assembled together, the tray 34 isolates each individual core from other cores in the array 33. Each core has a small hole 33a provided through it in a longitudinal direction from the upper surface through its base surface. A resistance heater array 35 is disposed at the base of the core array 33. The heater array 35 includes a number of individually actuable heater elements corresponding to the number of and positioned in register with the individual cores in the solid-form core array 33. When assembled, each core in the array 33 is in contact (or positioned adjacent) at its base with a respective resistance heater element in the heater array 35. A porous filter 36 is disposed at the top of the core array 33. The filter 36 allows the passage of gas generated from the solid-form cores into the headspace of the gas generator 32 located above the filter, while filtering out solid particles.

To generate the corresponding gas from the solid-form cores in the array 33 (e.g. to generate oxygen from $NaClO_3$ in the illustrated embodiment), the resistance heater elements in the heater array 35 can be individually and sequentially energized to initiate a decomposition reaction of the associated solid-form core(s) to produce the resultant gas. In the case of $NaClO_3$, heating the core above 250° C. initiates a decomposition reaction that produces oxygen gas ($O_2$) and solid sodium chloride. Because the core is initially heated at its base surface, the decomposition reaction begins there. Gaseous oxygen produced therefrom proceeds upward through the hole 33a in the respective solid core, through the filter 36 and into the headspace of the gas generator 32. This continues until the core has been exhausted; i.e. fully decomposed to produce $O_2$ and NaCl. The headspace is dimensioned and constructed so as to withstand the pressure from oxygen gas generated from the decomposition of at least one solid-form core. A microchannel fitted with a check valve (not illustrated) provides fluid communication between the headspace of the gas generator 32 with the interior volume of the experiment vessel 42. The check valve permits gas flow only in the direction from the gas generator to the experiment vessel. The vessel 42 is preferably initially pressurized to slightly above atmospheric pressure with oxygen, at a lower pressure than the head pressure in the headspace of the gas generator 32 as a result of gas evolution from decomposition of the solid-form core. Consequently, gas evolved in the gas generator 32 proceeds into the vessel 42 via the aforementioned microchannel due to a pressure gradient and without any mechanical pumping or pressurizing equipment. The microchannel preferably is long, composed of a low thermal conductivity material, and is thermally strapped to a structure that has a temperature between those of the gas generator and experiment tank, such that it does not provide a substantial pathway for conducting thermal energy into the experiment vessel 42 from warmer parts of the picosatellite 1.

Once one solid-form core in the array 33 has been fully decomposed, a second resistance heater in the heater array 35 can be actuated to begin the decomposition of a second solid-form core to generate additional gas, e.g. oxygen, which will again be conducted into the experiment vessel 42 as described above. Successive cores can be similarly heated and decomposed sequentially until the desired amount of gas has been delivered into the experiment vessel 42. By providing the solid-form source material as an array of relatively small and individually decomposable cores, the rate of gas generation can be regulated to ensure the gas pressure generated in the headspace of the gas generator 32 and in the experiment vessel 42 does not exceed safety limits.

The experiment vessel 42 is located in the experiment section 40 of the picosatellite 1 as described above. Preferably, the vessel 42 is suspended at the center of the experiment section 40 by a plurality of low-conductivity cords or wires 44 tensioned between points along the exterior surface of the vessel 42 and the frame 10. For example, the vessel 42 can be suspended from eight such cords 44 extending from each of the eight respective interior corners of the experiment section 40 to respectively aligned points along the vessel 42 exterior surface. If desired, heat-transfer fins 45 (seen in FIG. 3a, discussed below) can also be provided mounted to the exterior surface of the vessel 42 to improve heat-transfer efficiency from the vessel 42 into the heat-sink of space. Thermal insulation 38 is disposed in the experiment section 40 above the experiment vessel 42 to shield it from the source section 30 and the gas generator 32. The thermal insulation 38 preferably is conventional mylar (i.e. biaxially-oriented polyethylene terephthalate) insulation, such as aluminized (e.g. double-aluminized) mylar film. The film layers are stacked on top of one another to fill the available space above the experiment vessel 42 within the experiment section 40. In a preferred embodiment, the portion of the frame 10 defining the experiment section 40 is distinct from the remainder of the satellite frame 10, and is spaced therefrom via low-conductivity stand-offs, e.g. disposed at each of the four corners of the frame. The space provided by the stand-offs can be filled with the stacked mylar insulation 38.

In an illustrative embodiment, each of the four side walls of the experiment section includes a louver 43 that is actuable between an open position as illustrated in FIG. 1, and a closed position. In the closed position, the louver 43 pivots downward from its point of attachment to the frame 10 to close off the opening in the frame through which the enclosed experiment vessel 42 is otherwise exposed to the ambient environment. Each of the louvers 43 is individually actuable to be either open or closed. In the illustrated embodiment, the louvers 43 are mounted via hinges that are spring-biased in an open position and a tensile cord 43a is connected to a terminal portion of each louver 43, distal from where it is hingedly attached to the frame 10. The louvers 43 can be individually closed by tensioning the cord 43a to thereby pivot the louver 43 into the closed position against the spring-bias of its hinge. The cord 43a can be tensioned, for example, via a respective servo motor 43b located in the bus section 20 of the picosatellite 1. It is desirable to locate the servo motors 43b in the bus section 20, distant from the experiment section 40, to minimize as much as possible heat transfer from the motors 43b into the experiment vessel 42.

In directions facing away from the Earth (and insulated from the sun), the vacuum of space provides a heat sink of approximately 3K. In operation, the individual louvers 43 are actuated so that those facing away from the Earth and shielded from the sun are open, thus exposing the vessel 42 to space and to a low-temperature heat sink. Conversely, louvers 43 facing the Earth are closed to shield the vessel 42 from Earth-sourced IR and reflected solar radiation, which would otherwise produce heat transfer into the vessel 42 and its contents, thus raising their temperature.

Optionally, the louvers 43 can be provided with a layer(s) or a coating(s) configured to transmit radiation from the experiment vessel 42 at its prevalent temperature, but to reflect Earth-sourced IR radiation as well as solar radiation (both direct and that reflected from the Earth) at applicable temperatures. For example, the peak wavelengths of the respective radiation waves can be determined via conventional techniques, and films designed to transmit peak wavelengths of radiation from the experiment vessel 42, yet to reflect peak wavelengths of Earth-sourced IR and reflected solar radiation, can be designed. According to one model, Earth-sourced IR has a peak wavelength of 2 microns, solar irradiation has a peak wavelength of around 500 nm, and radiation from the experiment vessel will have peak radiation around 10 microns in the case of liquid oxygen stored at ~100K. Thus, coatings can be designed to reflect relatively smaller wavelengths of 2 microns and below, while transmitting larger wavelengths around 10 microns. Such coatings can be custom designed and supplied by, e.g., Newport. In addition to the louvers 43, other surfaces in the experiment section 40, including the outer surface of the experiment vessel 42 itself, can be provided with selectively-reflective coatings. As a result, lower steady-state temperature may be achieved for the experiment vessel because radiation tending to raise its temperature will be inhibited, whereas radiation from the vessel to the heat-sink of space will be permitted.

The vessel 42 is maintained at a low temperature via exposure to the heat-sink of space. Mathematical modeling has determined that by balancing the heat-sink effect of space against the inevitable heat leak into the vessel 42 from thermal sources such as the Earth, the sun and other heat-generating components onboard the picosatellite 1 (e.g. the control features in the bus section 20), the disclosed picosatellite 1 design can maintain a steady-state temperature of approximately 100K (+/−5K or 10K) in the experiment vessel 42 without active refrigeration in the case of storing liquid oxygen.

Due to the vessel's 42 low temperature, gas delivered thereto from the gas generator 32 will begin to condense at the interior wall of the vessel 42 once its boiling point exceeds the wall temperature (~100K) at the prevalent pressure; i.e. once its vapor pressure is reached at the prevalent temperature. For example, the vapor pressure of oxygen at 100K is approximately 150 psia. Accordingly, in the illustrated configuration once sufficient oxygen has been delivered to the experiment vessel 42 to produce a pressure of 150 psia, liquid oxygen will begin to condense at the vessel wall. Oxygen can then continue to be delivered to the vessel, resulting in continued condensation and formation of cryogenic liquid oxygen, until the solid-form source material (in this case $NaClO_3$) in the gas generator 32 has been exhausted. In this regard, another benefit of the sequential decomposition of successive solid-form cores in the gas generator 32 to form oxygen will be recognized: the condensation of gaseous oxygen to liquid in the experiment vessel 42 can take some time. By metering the delivery of oxygen from sequentially decomposed solid-form cores, instead of supplying all the oxygen at once, excessive pressure build-up can be avoided while gaseous oxygen is condensing.

Figure 3:
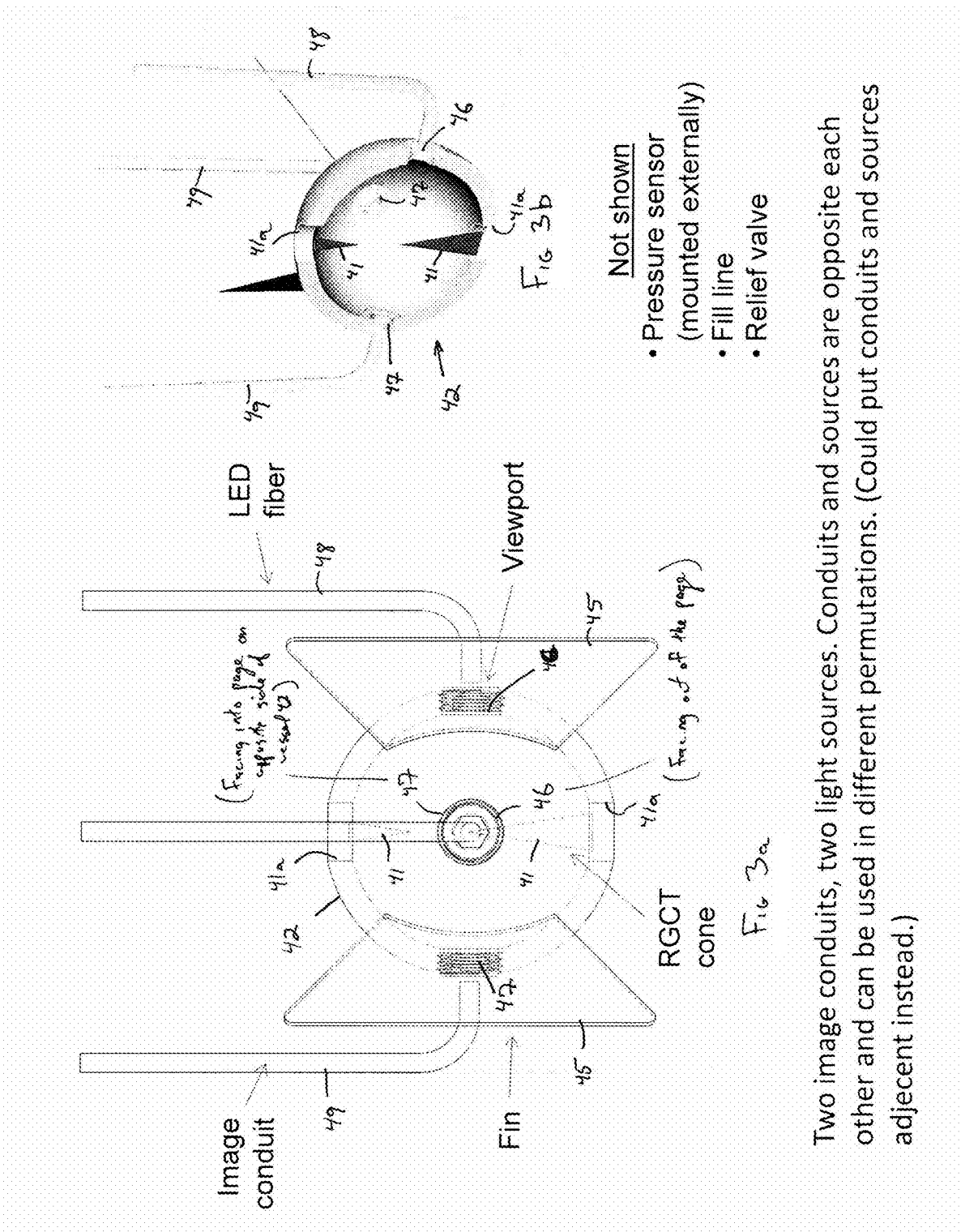
FIG. 3A shows a side view of an experiment vessel provided with at least one sensor and a camera arranged adjacent to a viewing port of an experiment vessel.
FIG. 3B shows another side view of the experiment vessel appearing in FIG. 3A.

FIGS. 3a and 3b show close-up views of the experiment vessel 42 illustrating instrumentation thereof. FIG. 3a is a side schematic view and FIG. 3b is a perspective section view, with half of the vessel removed to provide a view of the interior. Preferably, the vessel 42 is fitted with means to illuminate and visualize its contents. In the illustrated embodiment four visualization/illumination ports are disposed in the wall of the spherical vessel 42, disposed in a bisecting plane and distributed at spaced 90° intervals about the vessel's circumference. Two of these ports are illumination ports 46 and two of them are visualization ports 47. Referring to FIG. 3a, illumination is provided into the experiment vessel 42 via light from a light-emitting diode located in the bus section 20. The light is conducted down through the satellite frame 10, into the experiment section and ultimately into the vessel 42 via a fiber-optic lighting conduit 48. The fiber-optic lighting conduit 48 can be provided so that its terminal portion, from which light will be emitted, is disposed inside the vessel 42 just inside its wall through a conventional fitting mated with the port 46 and capable to withstand cryogenic temperatures and the prevalent pressures. Alternatively, the terminal portion of the fiber-optic lighting conduit 48 can be disposed outside the vessel wall, wherein the port 46 includes an optically-transparent window capable of transmitting light from the fiber into the vessel interior. In this embodiment, the window can be made from, e.g., quartz or sapphire, and may be provided as a pre-fabricated transparent lens within a conventional fitting that can be screwed into a complementary fitting provided in the vessel 42 wall (port 46) to ensure a leak-tight seal.

Visualization can be achieved using a conventional camera sensor. The camera sensor and its associated circuitry can be disposed in the bus section 20. The camera sensor is connected to a fiber-optic imaging conduit 49 that extends along the length of the satellite frame 10 such that its distal end is disposed adjacent another window disposed in the visualization port 47. Here, the window is provided as a pre-fabricated lens that is fitted into the port 47 and whose focal length is selected to focus the camera sensor, via the fiber-optic imaging conduit 49, on the interior of the vessel 42 to provide real-time visualization of the vessel contents. The camera sensor preferably will be capable of providing both still and moving images of the vessel contents, and will be connected to control circuitry and a physical memory to store image and video data for transmission to a remote (e.g. ground-based) control center. Preferably, the vessel 42 is fitted with at least two imaging conduits 49 connected to respective camera sensors (via different visualization ports), and at least two lighting conduits 48 connected to respective LEDs (via different illumination ports 46) to provide at least two vantage points from which to record image data, as well as a variety of lighting options to provide desired lighting contrast to effect proper visualization.

The experiment vessel 42 can be fitted with at least one, and optionally two or more, liquid-level sensor assemblies 41. According to illustrative embodiments, the liquid level sensor assemblies 41 are as disclosed in U.S. patent application Ser. No. 12/860,394 filed Aug. 20, 2010, the contents of which are incorporated herein by reference in their entirety. Briefly, each sensor assembly 41 includes a main body, a sensor, and a filler. The main body includes an outer surface having a continuously-variable radius of curvature in at least one portion. A sensor (e.g. a diode) is disposed in the assembly recessed from the outer surface. The sensor is in thermal communication with a region of that surface having relatively low radius of curvature. Liquid droplets adhered to the outer surface in this region will tend to migrate to a distant location having a higher radius of curvature via surface-tension effects. The main body has low thermal conductivity. The filler has a relatively higher thermal conductivity and, in embodiments, fills an opening in the outer surface of the main body and provides a thermally-conductive pathway between the sensor and the surrounding environment via the opening. The presence or absence of liquid in the vicinity of the opening (e.g. in thermally-conductive contact with the sensor) is determined based on how quickly thermal energy generated by applying a voltage to the sensor is dissipated. If liquid is in thermal contact with the sensor via a conductive pathway, then thermal energy generated by applying a voltage to the sensor will dissipate more rapidly compared to if no liquid is in such contact. The non-conductive body is made of a non-conductive material and therefore has low thermal mass. This ensures that thermal energy is not dissipated to a great extent into that body itself. Instead, the dissipation of thermal energy generated at the sensor (e.g. diode) is concentrated along a conductive pathway through the filler, including its exposed portion in contact with the environment, and the rate of thermal-energy dissipation depends on whether there is a thermal sink in contact with the conductive pathway to absorb the energy. Liquid has a relatively high density and high thermal mass compared to gas or vapor (or vacuum). Consequently, the rate of thermal dissipation from the sensor will be greater if liquid is in contact with the conductive pathway to the sensor (filler) than if gas or vapor (or vacuum) is in contact with that pathway. As will be appreciated, in the case of sensor being a diode, the energy-dissipation rate will affect the temperature of the diode, which in turn will affect the voltage measured for the diode. Therefore, measuring the voltage of a diode used as the sensor provides an indication of temperature. Measuring that voltage continuously or at selected intervals provides an indication of thermal-dissipation rate, which can be correlated to whether liquid is or is not in thermal contact (e.g. via a conductive pathway, such as via the exposed portion of filler) with the diode.

In the illustrated embodiment, two liquid level sensor assemblies 41 are illustrated mounted to the interior of and extending into the experiment vessel 42 at diametrically-opposed locations along a centerline normal to the plane of the visualization/illumination ports 46, 47. Respective sensor ports 41a are disposed in the vessel 42 wall along this line to provide a pathway for feeding control wires to the sensor assemblies 41. In addition, one of these sensor ports 41a can provide a pathway for additional instrumentation, e.g. an externally mounted or disposed pressure transducer for providing pressure measurement within the vessel 42. One of the sensor ports 41a can also provide a pathway for passage of a fill line from the gas generator 32 into the experiment vessel 42. Alternatively, distinct ports can be provided in the vessel 42 wall to permit passage of the fill line or additional instrumentation.

As will be appreciated, it is preferred that all processing and control hardware and systems, as well as all instrumentation systems to the extent possible, are located remote from the experiment section 40 to minimize heat transfer into the experiment vessel. Thus, energized instrumentation elements that may generate heat, such as pressure transducers, camera sensors, LEDs, etc., preferably are disposed distant from the experiment section 40 in the bus section 20, and connected to the experiment vessel 42 via low-conductivity wires, conduits or optical fibers. Such wires and fibers can be strung along the length of the picosatellite 1, e.g. along its frame 10 between the bus section 20 and the experiment section 40.

Figure 4:
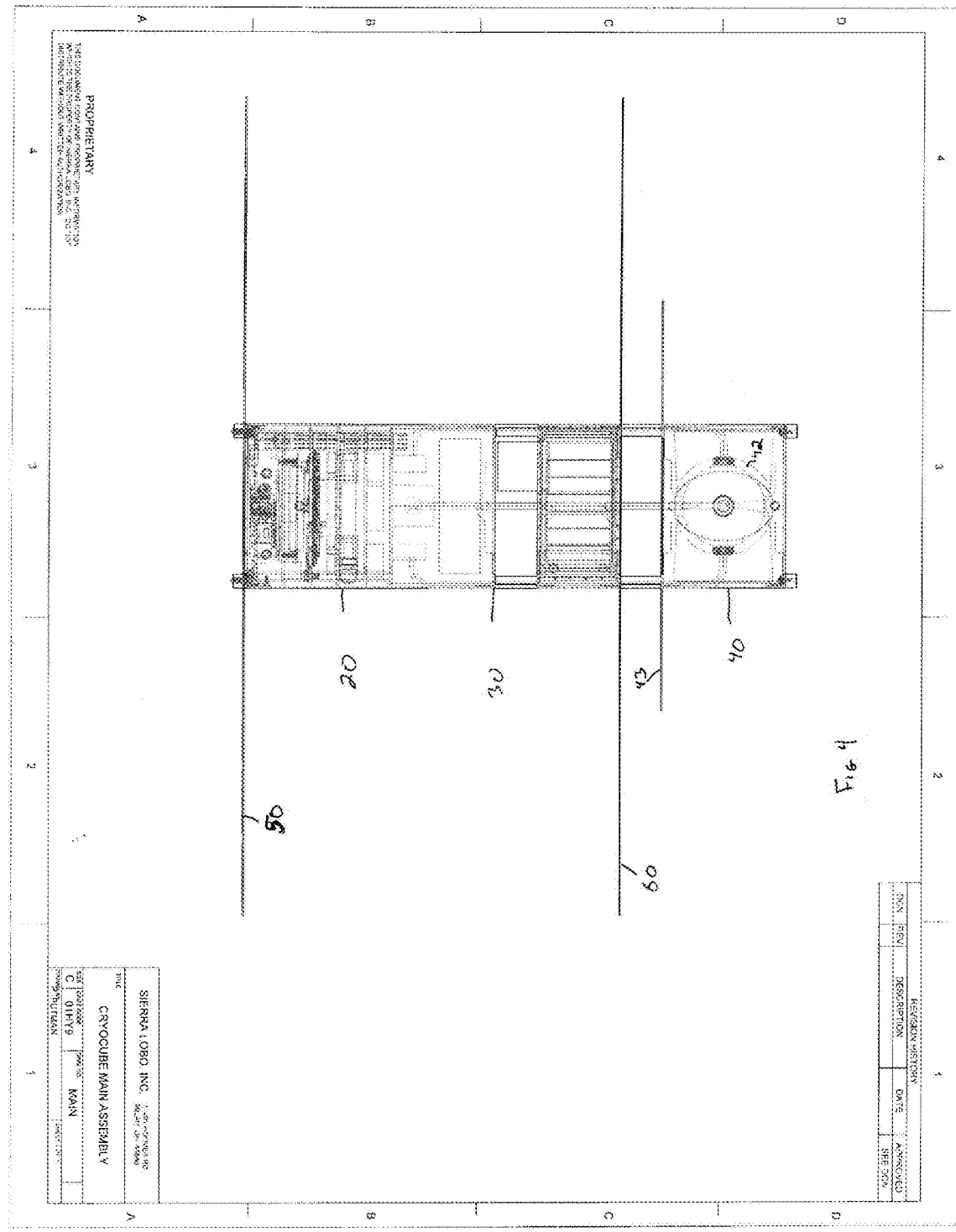
FIG. 4 shows a partially-cutaway side view of an embodiment of a picosatellite with a Sun shield, an Earth shield and a louver in their deployed states.
Figure 5:
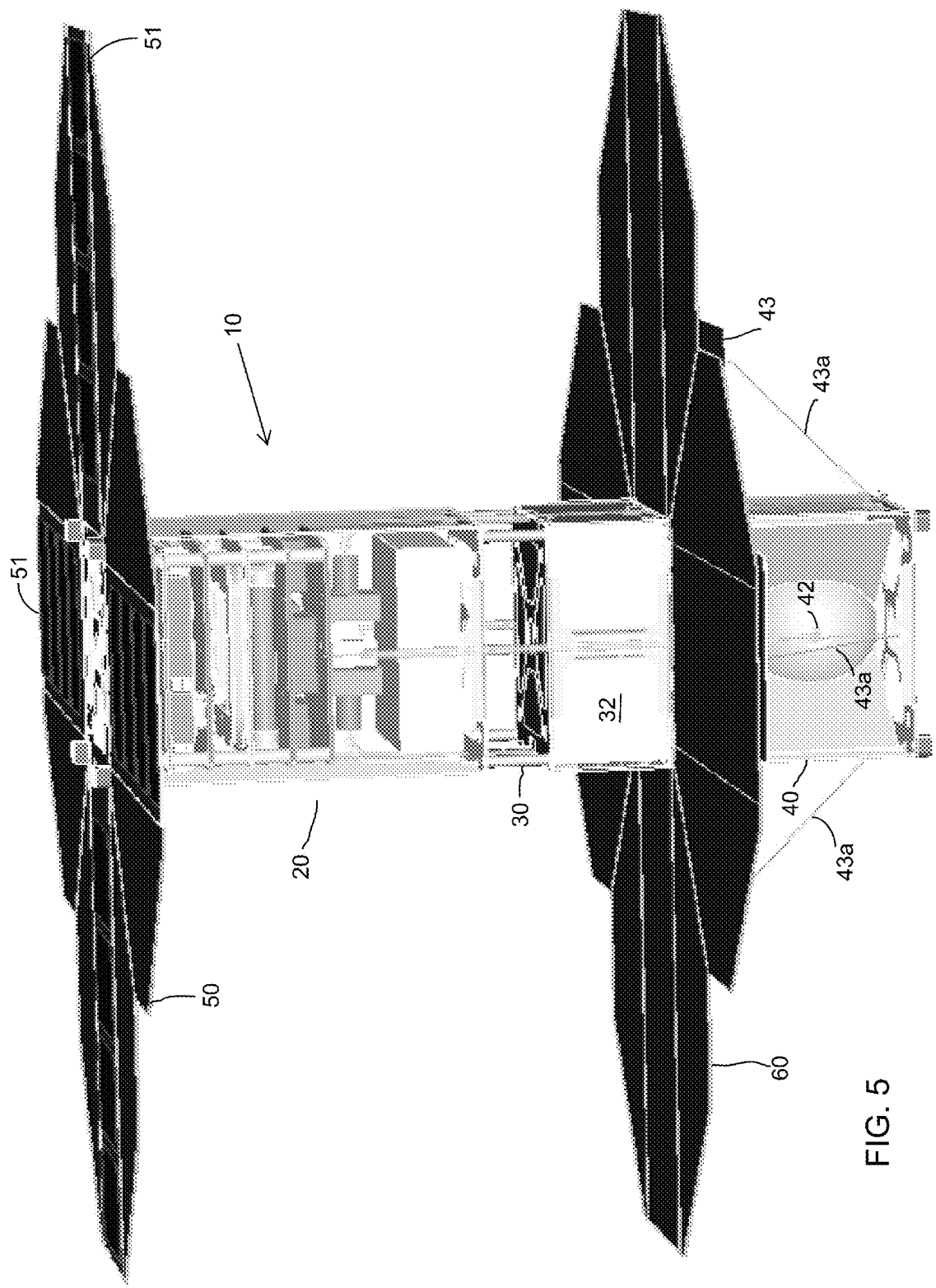
FIG. 5 shows a partially-cutaway side view of an embodiment of a picosatellite with a Sun shield, an Earth shield and a louver in their deployed states.
Figure 6:
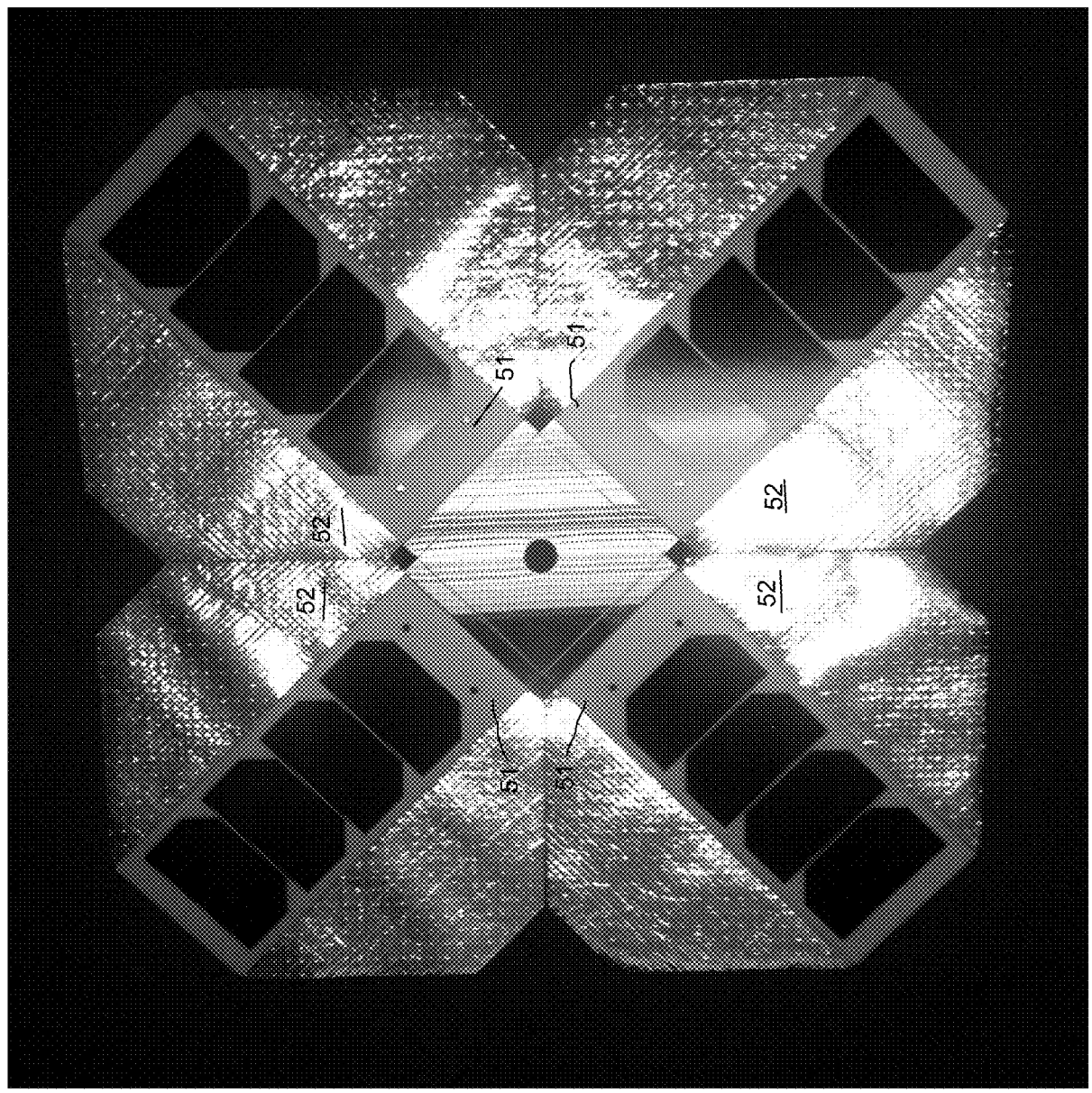
FIG. 6 shows a top view of panels collectively forming a deployed Sun shield.

Referring now to FIGS. 1, 4 and 5, the picosatellite 1 includes a sun shield 50 disposed at the upper portion of the frame 10, to shield the picosatellite 1 (including the bus section 20, the source section 30 and the experiment section 40) from direct solar irradiation. A top view of the sun shield 50 is shown in FIG. 6. The sun shield 50 includes a substantially square layer (or laminate) of insulating film(s) 52, which can be aluminized or double-aluminized mylar film(s) as known in the art capable of reflecting solar rays. The insulating film(s) 52 is/are fitted over and adhered to four rectangular panels 51 (best seen in FIG. 6), which are hingedly connected along respective proximal edges thereof to an upper portion of the frame 10 at the top of the bus section 20. The rectangular panels 51 are spring-biased into an open (i.e. deployed) configuration as seen in the aforementioned figures. In this deployed configuration, the attached insulating film(s) 52 is/are fully unfolded to present a substantially flat, planar sun shield to protect the picosatellite 1 from direct solar irradiation. Once deployed, the picosatellite 1 is attitude-controlled to ensure that the sun shield always faces the sun while orbiting the Earth. To accommodate the CubeSat 1 launcher, however, sun shield 50 is initially in an un-deployed or stowed configuration as seen in FIG. 7. In this configuration, the panels 51 are hinged downward and disposed substantially parallel to and adjacent the sides of the satellite frame 10, with the insulating film(s) 52 of the sun shield folded underneath the panels 51. In this configuration the entire picosatellite 1 will fit inside the CubeSat 1 launcher. Upon deployment from that launcher, a control signal from an onboard microprocessor, or transmitted from a remote control center, can trigger deployment of the sun shield; e.g. release of a latch or latches (not shown) holding the panels 51 in the stowed configuration, so that the biasing force acting on the panels or their hinges will swing the panels 51 into the deployed configuration shown in FIG. 5. As the panels 51 swing into the deployed configuration, the attached insulating film(s) 52 unfold(s) and present(s) the substantially planar sun shield 50 as illustrated. The film(s) 52 are subdivided and shaped so that the width of the subsections is less than the width of the panels 51, making it possible to stow the film(s) without blocking rails that must mate with the CubeSat 1 launcher as seen in the figure immediately below.

The outer surfaces of the panels 51 (i.e. facing away from the picosatellite 1 and toward the sun during operation) may be provided with one or a plurality of photocells 53, which can absorb solar radiation and convert it into electrical energy to power the picosatellite 1 subsystems in a conventional manner.

The picosatellite 1 also includes an Earth shield 60, an embodiment of which is again as seen in FIGS. 1, 4 and 5. The Earth shield 60 can be configured and biased in a deployed configuration similarly as the sun shield 50 described above, except that the panels of the Earth shield will be hinged from the satellite frame 10 at a location between the gas-generation and experiment sections 30 and 40, such that when stowed they are disposed substantially parallel to and against the satellite frame 10, pivoted toward the bus section 20. Thus, when fully stowed for launch the Earth shield 60 is stowed against the satellite frame 10 and the sun shield 50 is stowed against the subjacent (and stowed) Earth shield 60. On deployment of the picosatellite 1 in orbit both the sun shield 50 and Earth shield 60 can be deployed through action of their respective deploy-biasing forces once the counterforce preventing deployment (e.g. via electrically- or mechanically-actuated latches) is removed. Optionally, the Earth shield can have a selectively-reflective coating(s) or layer(s) as discussed above, configured to transmit peak wavelengths of irradiation from the experiment vessel 42 but to reflect peak wavelengths of Earth-sourced IR and direct/reflected solar irradiation.

Figure 9:
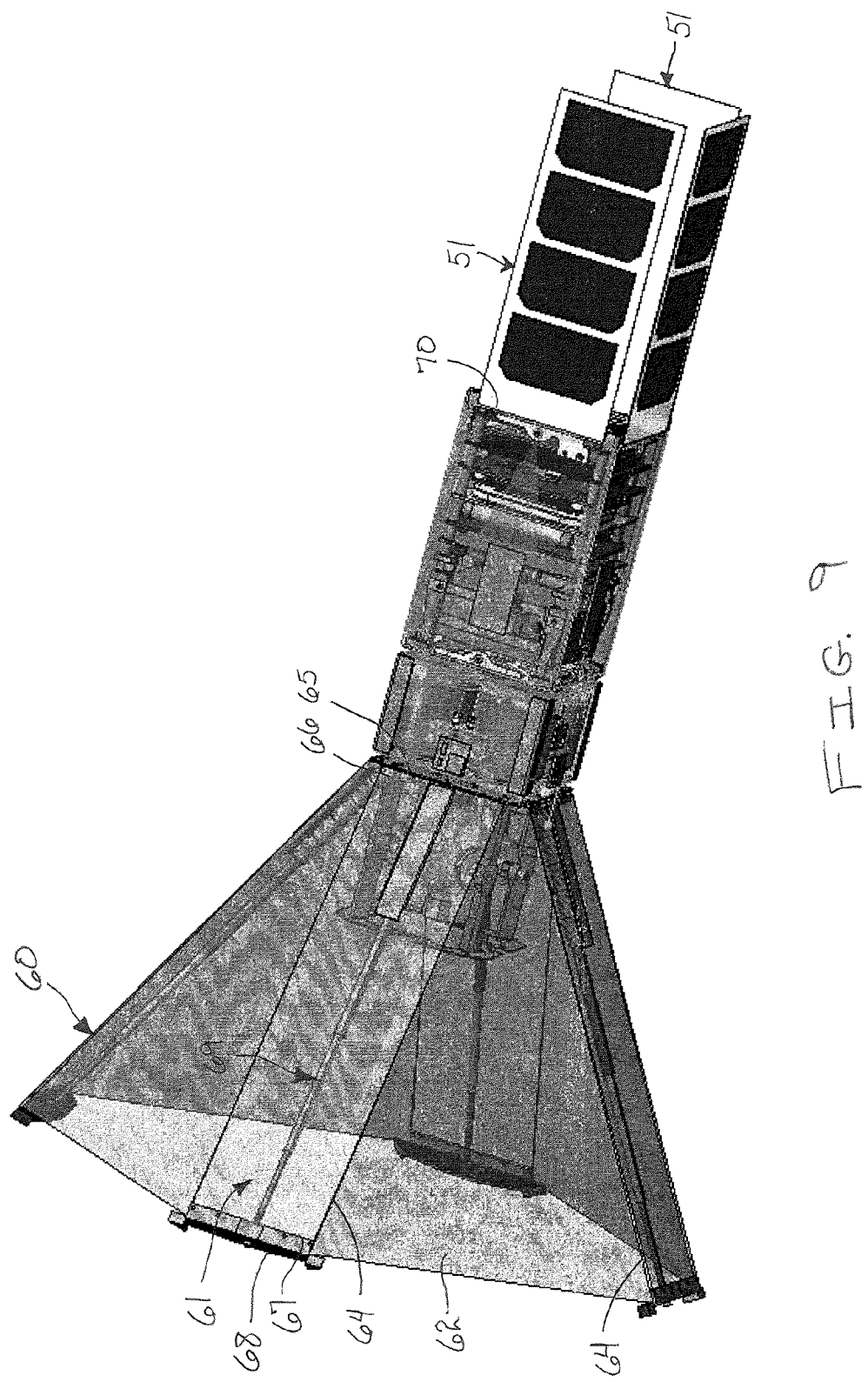
FIG. 9 offers a perspective view of a picosatellite with an Earth shield deployed to continuously extend circumferentially about the entire periphery of an experiment vessel.

An alternate embodiment of the Earth shield 60 is shown in FIG. 9. Similar to the embodiments described above, the Earth shield 60 of the present embodiment can be configured and biased in a deployed configuration similarly as the sun shield 50, such that the panels 61 of the Earth shield are hinged from, or flexibly coupled to the satellite frame 10 at a location between the source section 30 and the experiment section 40. Unlike the previous embodiments, however, the panels 61 can be formed from a sheet of suitably-reflective material such as mylar film attached at a proximate end 66 to the satellite frame 10, and at a distal end 67 to a cross member 68. The cross member 68 is coupled to the end of a telescopically-extendable arm 69 that is pivotally coupled to the satellite frame 10 adjacent to the experiment section 40. The arm 69 includes a plurality of segments each having a different diameter. An arm segment with a relatively-small diameter can be telescopically received within an interior passage defined by an arm segment having a relatively-large diameter. A compression spring extends between each of the plurality of arm segments to naturally bias each arm segment outwardly away from an underlying arm segment located closer to the experiment section 40. In the absence of any mechanism counteracting the biasing force exerted by the springs, the arm 69 is fully extended such that the cross member 68 is positioned outwardly, generally away from the satellite frame 10.

When stowed, the panels 61 are disposed substantially parallel to and against the satellite frame 10, pivoted toward the bus section 20, to allow the picosatellite 1 to fit within the launcher. According to such embodiments, the flexible mylar film sheet or other flexible material can be folded for stowage between the panels 51 of the sun shield 50. According to other embodiments, the flexible mylar film or other flexible material forming the panels 61 can be wrapped around a spool coupled to the satellite frame 10, and unwound as the arms 69 are extended when the picosatellite 1 is deployed. Regardless of how the panels 61 are coupled to the satellite frame 10 to be stowed, the arm segments forming each of the plurality of arms 69 are compressed such that the length of the panels 61 does not extend beyond the overall length of the satellite frame 10. This allows the panels 51 of the sun shield 50 to be pivotally adjusted about their respective hinges 70 to conceal the underlying material forming the panels 61. Thus, when fully stowed for launch the Earth shield 60 is stowed against the satellite frame 10 and the sun shield 50 panels 51 are stowed against the subjacent (and stowed) panels 61 of the Earth shield 60. A flexible film 62 of reflective material such as mylar, for example, extends between opposing edges 64 of immediately adjacent panels 61. While the panels 61 of the Earth shield 60 are stowed, the films 62 between panels 61 are also folded and maintained between the satellite frame 10 and the respective panels 61.

On deployment of the picosatellite 1 in orbit both the sun shield 50 and Earth shield 60 can be deployed through action of their respective deploy-biasing forces once the counterforce preventing deployment (e.g. via electrically- or mechanically-actuated latches) is removed. Optionally, the panels 61 of the Earth shield 60 can have a selectively-reflective coating(s) or layer(s) as discussed above, configured to transmit peak wavelengths of irradiation from the experiment vessel 42 but to reflect peak wavelengths of Earth-sourced IR and direct/reflected solar irradiation. In response to removal of the counterforce preventing deployment, each panel 61 and its respective arm 69 are urged by a torsion spring or other biasing mechanism to rotate about a hinge 65 pivotally connecting the panel 61 adjacent to the satellite frame 10 near the experiment section 40. Any force resisting the biasing force of the springs provided to the arm segments is also released upon deployment of the picosatellite 1, thereby allowing full extension of the arms 69 to pull the material forming the panels 61 taut. In their fully deployed orientation, each panel 61 is rotated beyond 90° about the hinge 65 from their stowed orientation. Fully deployed, the cross member 68 is positioned longitudinally beyond the terminal edge of the experiment section 40. In other words, the experiment section 40 appears to be recessed within a cavity defined by the surrounding Earth shield 60. Accordingly, the present embodiment forms a substantially octagonal-shaped cone with the experiment section 40 located adjacent to the apex of the cone.

The picosatellite 1 preferably utilizes magnetic attitude control to keep the sun shield 50 oriented toward the sun with the experiment section distant-most from the sun. The magnetic attitude-control hardware can regulate the attitude of the picosatellite 1 based on the applied magnetic field of the Earth. Such control hardware can be conventional. The picosatellite 1 optionally can include a vibratory motor, preferably mounted in the bus section, to deliver vibrations to the picosatellite 1 and ultimately to the experiment vessel 42. Such vibrations can be used to generate sloshing of the cryogenic liquid in the vessel 42 in order to observe and evaluate its behavior during sloshing in microgravity. The vibratory motor can be, e.g., conventional electric motor having a rotating shaft, with a weight fitted eccentrically to the shaft so that as the shaft rotates the eccentric weight causes the motor, and the picosatellite 1 to which it is mounted, to vibrate. Alternatively, the vibratory motor can be a reciprocating motor, such that a reciprocating member of sufficient mass results in vibration as a result of such reciprocation.

Due to its small size, small mass and capability to be launched as a secondary payload (i.e. no liquid cryogens requiring refrigeration or gases at high pressure during launch), the disclosed picosatellite 1 provides a platform for space-based evaluation of cryogenic-liquid behavior in microgravity at a fraction of the cost of launching a conventional satellite as a primary payload. When oxygen is the cryogen to be tested no onboard refrigeration will be necessary because space provides an adequate heat sink to condense gaseous oxygen within the experiment vessel 42 as discussed above. For lower-boiling cryogens, e.g. hydrogen, an onboard refrigerator may be required. But for the small volumes in the present picosatellite 1 (e.g. the experiment vessel 42 itself fits within a 10 cm3 cube), it is contemplated that a relatively small refrigerator of only 1-2 W of refrigeration power would be required.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A testbed for conducting an experiment in a microgravity environment on a substance in a cryogenic liquid state, the testbed comprising:
   a source section comprising a storage tank that stores a compressed gas comprising the substance to be evaluated in the cryogenic liquid form;
   an experiment section comprising an experiment vessel in fluid communication with the storage tank to receive the compressed gas from the storage tank and condense the compressed gas into the cryogenic liquid state;
   a sensor adapted to sense a property of the cryogenic liquid in the experiment vessel as part of the experiment in the microgravity environment; and
   a bus section comprising a controller configured to control delivery of the compressed gas from the storage tank to the experiment vessel, and to receive property data indicative of the property sensed by the sensor for subsequent evaluation on Earth,
   all of said source section, said experimental section and said bus section being disposed in a frame having rectangular nominal dimensions.

2. The testbed of claim 1, wherein the nominal dimensions of the frame are no greater than: 100 mm wide, 100 mm high, and 340.5 mm long.

3. The testbed of claim 1, wherein the source section comprises a plurality of storage tanks, each storing the compressed gas to be delivered to the experiment vessel as controlled by the controller.

4. The testbed of claim 3, wherein the controller is adapted to control delivery of the compressed gas from each of the storage tanks to the experiment vessel in a sequential manner.

5. The testbed of claim 1 further comprising a sun shield coupled to the frame at a location to be deployed once the testbed is placed in Earth orbit to shield the experiment section from solar radiation.

6. The testbed of claim 5, wherein the sun shield is coupled to the frame at a location adjacent to a first terminal end of the frame along a longitudinal axis, opposite a second terminal end of the frame adjacent to the experiment vessel.

7. The testbed of claim 1 further comprising an Earth shield coupled to the frame adjacent to the experiment vessel, the Earth shield comprising a plurality of adjustable panels that, when fully deployed, at least partially define a cavity in which the experiment vessel is recessed.

8. The testbed of claim 7, wherein each of the plurality of panels comprises a sheet of flexible material extending between the frame and a distal end of an arm having an adjustable length.

9. The testbed of claim 7 further comprising sheets of flexible material that extend between immediately-adjacent panels to form a continuous Earth shield that extends circumferentially about the experiment vessel in its entirety.

10. The testbed of claim 7 further comprising an adjustable louver disposed along the frame between the experiment vessel and the Earth shield, wherein the adjustable louver is adjustable between a stowed arrangement adjacent to the frame and a deployed arrangement in which the adjustable louver extends outwardly, generally away from the frame.

11. The testbed of claim 1 further comprising a camera arranged to capture an image of the cryogenic liquid within the experiment vessel, wherein the camera is operatively connected to transmit data indicative of the image to the controller.

12. The testbed of claim 1, wherein the sensor is adapted to sense a temperature of the cryogenic liquid in the experiment vessel and/or a level of the cryogenic liquid in the experiment vessel.

13. The testbed of claim 1 further comprising:
   a sun shield coupled to the frame at a location adjacent to a first terminal end of the frame along a longitudinal axis to be deployed once the testbed is placed in Earth orbit to shield the experiment section from solar radiation;
   an Earth shield coupled to the frame adjacent to a second terminal end of the frame and the experiment vessel, the Earth shield comprising a plurality of adjustable panels that, when fully deployed, at least partially define a cavity in which the experiment vessel is recessed, wherein
      the controller is further configured to control an attitude of the testbed in Earth orbit to maintain a position of the sun shield between the Sun and the experiment vessel.

14. A testbed for conducting an experiment in a microgravity environment on a substance in a cryogenic liquid state, the testbed comprising:

a source section comprising a source material comprising the substance to be evaluated in the cryogenic liquid form;
an experiment section comprising an experiment vessel that receives the substance from the source material and condenses the substance into the cryogenic liquid state;
a sensor adapted to sense a property of the cryogenic liquid in the experiment vessel as part of the experiment in the microgravity environment;
a bus section comprising a controller configured to control delivery of the substance to the experiment vessel, and to receive property data indicative of the property sensed by the sensor for subsequent evaluation on Earth;
wherein all of said source section, said experimental section and said bus section are disposed in a frame having rectangular nominal dimensions; and
an Earth shield coupled to the frame adjacent to the experiment vessel, the Earth shield comprising a plurality of adjustable panels that, when fully deployed, at least partially define a cavity in which the experiment vessel is recessed.

15. The testbed of claim 14, wherein each of the plurality of panels comprises a sheet of flexible material extending between the frame and a distal end of an arm having an adjustable length.

16. The testbed of claim 15 further comprising sheets of flexible material that extend between immediately-adjacent panels to form a continuous Earth shield that extends circumferentially about the experiment vessel in its entirety.

17. The testbed of claim 14, wherein the nominal dimensions of the frame are no greater than: 100 mm wide, 100 mm high, and 340.5 mm long.

18. The testbed of claim 14, wherein the source section comprises a gas generator that generates a gas comprising the substance from a solid source material in response to a control signal issued by the controller.

19. The testbed of claim 18, wherein the controller is adapted to control delivery of the gas from a plurality of different solid source materials in a sequential manner.

* * * * *